(12) United States Patent
Milliman

(10) Patent No.: US 9,504,470 B2
(45) Date of Patent: *Nov. 29, 2016

(54) CIRCULAR STAPLING DEVICE WITH BUTTRESS

(71) Applicant: Covidien LP, Mansfield, MA (US)

(72) Inventor: Keith L. Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 492 days.

This patent is subject to a terminal disclaimer.

(21) Appl. No.: 14/156,713

(22) Filed: Jan. 16, 2014

(65) Prior Publication Data

US 2014/0239046 A1  Aug. 28, 2014

Related U.S. Application Data

(60) Provisional application No. 61/768,661, filed on Feb. 25, 2013.

(51) Int. Cl.
*A61B 17/04* (2006.01)
*A61B 17/10* (2006.01)
(Continued)

(52) U.S. Cl.
CPC ..... *A61B 17/1155* (2013.01); *A61B 17/07292* (2013.01)

(58) Field of Classification Search
CPC .............. A61B 17/07271; A61B 17/07292; A61B 17/0684; A61B 17/1155; A61B 17/11; A61B 2017/00473; A61B 2017/07214; A61B 2017/07271; A61B 2017/07257; Y10T 29/49815
USPC ........... 227/175.1–182.1; 606/139, 153–154, 606/219
See application file for complete search history.

(56) References Cited

U.S. PATENT DOCUMENTS

| 3,054,406 A | 9/1962 | Usher |
| 3,079,606 A | 3/1963 | Bobrov |

(Continued)

FOREIGN PATENT DOCUMENTS

| CA | 2 667 434 | 5/2008 |
| CN | 101310680 A | 11/2008 |

(Continued)

OTHER PUBLICATIONS

European Examination Report issued in corresponding European Appln. No. 14156342.9 dated Mar. 30, 2016.
(Continued)

*Primary Examiner* — Robert Long

(57) ABSTRACT

The cartridge assembly includes a housing, a pusher member, a fastener cartridge body, a circular cartridge buttress member, and a retaining ring member. The pusher member is supported within the housing and movable between a first position and a second position. The fastener cartridge body is supported on the housing and has a tissue engaging surface that extends to an annular edge. One or both of the housing and the fastener cartridge body define an annular containment groove. The circular cartridge buttress member has a body portion and an extension portion. The body portion is supported on the tissue engaging surface of the fastener cartridge body. The extension portion extends from the body portion and over the annular edge of the tissue engaging surface. The retaining ring member is secured within the containment groove to releasably secure the extension portion of the circular cartridge buttress member to the cartridge assembly.

15 Claims, 5 Drawing Sheets

(51) Int. Cl.
*A61B 17/115* (2006.01)
*A61B 17/072* (2006.01)

(56) References Cited

U.S. PATENT DOCUMENTS

| | | | |
|---|---|---|---|
| 3,124,136 A | 3/1964 | Usher |
| 3,490,675 A | 1/1970 | Green |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby |
| 4,655,221 A | 4/1987 | Devereux |
| 4,834,090 A | 5/1989 | Moore |
| 4,838,884 A | 6/1989 | Dumican |
| 4,927,640 A | 5/1990 | Dahlinder |
| 4,930,674 A | 6/1990 | Barak |
| 5,002,551 A | 3/1991 | Linsky |
| 5,014,899 A | 5/1991 | Presty |
| 5,040,715 A | 8/1991 | Green |
| 5,065,929 A | 11/1991 | Schulze |
| 5,205,459 A | 4/1993 | Brinkerhoff |
| 5,263,629 A | 11/1993 | Trumbull |
| 5,307,976 A | 5/1994 | Olson |
| 5,312,023 A | 5/1994 | Green |
| 5,314,471 A | 5/1994 | Brauker |
| 5,318,221 A | 6/1994 | Green |
| 5,326,013 A | 7/1994 | Green |
| 5,332,142 A | 7/1994 | Robinson |
| 5,344,454 A | 9/1994 | Clarke |
| 5,392,979 A | 2/1995 | Green |
| 5,397,324 A | 3/1995 | Carroll et al. |
| 5,405,072 A | 4/1995 | Zlock et al. |
| 5,425,745 A | 6/1995 | Green |
| 5,441,193 A | 8/1995 | Gravener |
| 5,441,507 A | 8/1995 | Wilk |
| 5,443,198 A | 8/1995 | Viola |
| 5,468,253 A | 11/1995 | Bezwada |
| 5,503,638 A | 4/1996 | Cooper |
| 5,542,594 A | 8/1996 | McKean |
| 5,549,628 A | 8/1996 | Cooper |
| 5,575,803 A | 11/1996 | Cooper |
| 5,653,756 A | 8/1997 | Clarke |
| 5,683,809 A | 11/1997 | Freeman |
| 5,690,675 A | 11/1997 | Sawyer |
| 5,702,409 A | 12/1997 | Rayburn |
| 5,752,965 A | 5/1998 | Francis |
| 5,762,256 A | 6/1998 | Mastri |
| 5,766,188 A | 6/1998 | Igaki |
| 5,769,892 A | 6/1998 | Kingwell |
| 5,782,396 A | 7/1998 | Mastri |
| 5,799,857 A | 9/1998 | Robertson |
| 5,810,855 A | 9/1998 | Rayburn |
| 5,814,057 A | 9/1998 | Oi |
| 5,833,695 A | 11/1998 | Yoon |
| 5,843,096 A | 12/1998 | Igaki |
| 5,871,135 A | 2/1999 | Williamson, IV et al. |
| 5,895,412 A | 4/1999 | Tucker |
| 5,895,415 A | 4/1999 | Chow |
| 5,902,312 A | 5/1999 | Frater |
| 5,908,427 A | 6/1999 | McKean |
| 5,915,616 A | 6/1999 | Viola |
| 5,931,847 A | 8/1999 | Bittner |
| 5,964,774 A | 10/1999 | McKean |
| 5,997,895 A | 12/1999 | Narotam |
| 6,019,791 A | 2/2000 | Wood |
| 6,030,392 A | 2/2000 | Dakov |
| 6,032,849 A | 3/2000 | Mastri |
| 6,045,560 A | 4/2000 | McKean |
| 6,063,097 A | 5/2000 | Oi |
| 6,080,169 A | 6/2000 | Turtel |
| 6,099,551 A | 8/2000 | Gabbay |
| 6,149,667 A | 11/2000 | Hovland |
| 6,155,265 A | 12/2000 | Hammerslag |
| 6,210,439 B1 | 4/2001 | Firmin |
| 6,214,020 B1 | 4/2001 | Mulhauser |
| 6,241,139 B1 | 6/2001 | Milliman |
| 6,258,107 B1 | 7/2001 | Balazs |
| 6,267,772 B1 | 7/2001 | Mulhauser |
| 6,273,897 B1 | 8/2001 | Dalessandro |
| 6,280,453 B1 | 8/2001 | Kugel |
| 6,299,631 B1 | 10/2001 | Shalaby |
| 6,312,457 B1 | 11/2001 | DiMatteo |
| 6,312,474 B1 | 11/2001 | Francis |
| 6,325,810 B1 | 12/2001 | Hamilton |
| 6,436,030 B2 | 8/2002 | Rehil |
| 6,454,780 B1 | 9/2002 | Wallace |
| 6,461,368 B2 | 10/2002 | Fogarty |
| 6,503,257 B2 | 1/2003 | Grant |
| 6,514,283 B2 | 2/2003 | DiMatteo |
| 6,517,566 B1 | 2/2003 | Hovland |
| 6,551,356 B2 | 4/2003 | Rousseau |
| 6,592,597 B2 | 7/2003 | Grant |
| 6,638,285 B2 | 10/2003 | Gabbay |
| 6,652,594 B2 | 11/2003 | Francis |
| 6,656,193 B2 | 12/2003 | Grant |
| 6,669,735 B1 | 12/2003 | Pelissier |
| 6,677,258 B2 | 1/2004 | Carroll |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois |
| 6,736,854 B2 | 5/2004 | Vadurro |
| 6,746,458 B1 | 6/2004 | Cloud |
| 6,773,458 B1 | 8/2004 | Brauker |
| 6,896,684 B2 | 5/2005 | Monassevitch |
| 6,927,315 B1 | 8/2005 | Heinecke |
| 6,939,358 B2 | 9/2005 | Palacios |
| 6,946,196 B2 | 9/2005 | Foss |
| 6,959,851 B2 | 11/2005 | Heinrich |
| 7,060,087 B2 | 6/2006 | DiMatteo |
| 7,087,065 B2 | 8/2006 | Ulmsten |
| 7,108,701 B2 | 9/2006 | Evens |
| 7,128,253 B2 | 10/2006 | Mastri |
| 7,128,748 B2 | 10/2006 | Mooradian |
| 7,134,438 B2 | 11/2006 | Makower et al. |
| 7,141,055 B2 | 11/2006 | Abrams |
| 7,147,138 B2 | 12/2006 | Shelton, IV |
| 7,160,299 B2 | 1/2007 | Baily |
| 7,210,810 B1 | 5/2007 | Iversen et al. |
| 7,232,449 B2 | 6/2007 | Sharkawy |
| 7,241,300 B2 | 7/2007 | Sharkawy |
| 7,307,031 B2 | 12/2007 | Carroll |
| 7,311,720 B2 | 12/2007 | Mueller |
| 7,377,928 B2 | 5/2008 | Zubik |
| 7,434,717 B2 | 10/2008 | Shelton, IV |
| 7,438,209 B1 | 10/2008 | Hess |
| 7,547,312 B2 | 6/2009 | Bauman |
| 7,559,937 B2 | 7/2009 | de la Torre |
| 7,571,845 B2 | 8/2009 | Viola |
| 7,594,921 B2 | 9/2009 | Browning |
| 7,604,151 B2 | 10/2009 | Hess |
| 7,665,646 B2 | 2/2010 | Prommersberger |
| 7,666,198 B2 | 2/2010 | Suyker |
| 7,669,747 B2 | 3/2010 | Weisenburgh, II |
| 7,717,313 B2 | 5/2010 | Bettuchi |
| 7,722,642 B2 | 5/2010 | Williamson, IV |
| 7,744,627 B2 | 6/2010 | Orban, III |
| 7,776,060 B2 | 8/2010 | Mooradian |
| 7,793,813 B2 | 9/2010 | Bettuchi |
| 7,799,026 B2 | 9/2010 | Schechter |
| 7,823,592 B2 | 11/2010 | Bettuchi |
| 7,824,420 B2 | 11/2010 | Eldridge |
| 7,845,533 B2 | 12/2010 | Marczyk |
| 7,845,536 B2 | 12/2010 | Viola |
| 7,846,149 B2 | 12/2010 | Jankowski |
| 7,892,247 B2 | 2/2011 | Conston |
| 7,909,224 B2 | 3/2011 | Prommersberger |
| 7,909,837 B2 | 3/2011 | Crows |
| 7,938,307 B2 | 5/2011 | Bettuchi |
| 7,942,890 B2 | 5/2011 | D'Agostino |

(56) References Cited

U.S. PATENT DOCUMENTS

| | | |
|---|---|---|
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,011,555 B2 | 9/2011 | Tarinelli |
| 8,016,177 B2 | 9/2011 | Bettuchi |
| 8,016,178 B2 | 9/2011 | Olson |
| 8,025,199 B2* | 9/2011 | Whitman ............. A61B 17/115 227/155 |
| 8,028,883 B2 | 10/2011 | Stopek |
| 8,038,045 B2 | 10/2011 | Bettuchi |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,127,975 B2 | 3/2012 | Olson et al. |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,178,746 B2 | 5/2012 | Hildeberg et al. |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,869 B2 | 4/2013 | Heinrich |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull |
| 8,474,677 B2 | 7/2013 | Woodard, Jr. |
| 8,479,968 B2 | 7/2013 | Hodgkinson |
| 8,485,414 B2 | 7/2013 | Criscuolo |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Stopek |
| 8,631,989 B2 | 1/2014 | Aranyi |
| 8,646,674 B2 | 2/2014 | Schulte et al. |
| 8,668,129 B2 | 3/2014 | Olson |
| 8,684,250 B2 | 4/2014 | Bettuchi |
| 8,721,703 B2 | 5/2014 | Fowler |
| 8,757,466 B2 | 6/2014 | Olson |
| 8,789,737 B2* | 7/2014 | Hodgkinson .... A61B 17/07207 227/176.1 |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2* | 3/2015 | Carter ................. A61B 17/072 227/176.1 |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2* | 4/2015 | Carter ............. A61B 17/07292 227/176.1 |
| 9,010,610 B2 | 4/2015 | Hodgkinson |
| 9,010,612 B2* | 4/2015 | Stevenson ........ A61B 17/07292 227/176.1 |
| 9,016,543 B2 | 4/2015 | (Prommersberger) Stopek |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2* | 8/2015 | Hodgkinson ........ A61B 17/1114 |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | (Prommersberger) Stopek et al. |
| 2002/0028243 A1 | 3/2002 | Masters |
| 2002/0091397 A1 | 7/2002 | Chen |
| 2002/0151911 A1 | 10/2002 | Gabbay |
| 2002/0165563 A1 | 11/2002 | Grant et al. |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian |
| 2003/0196668 A1 | 10/2003 | Harrison et al. |
| 2003/0208231 A1 | 11/2003 | Williamson, IV |
| 2004/0107006 A1 | 6/2004 | Francis |
| 2004/0254590 A1 | 12/2004 | Hoffman |
| 2004/0260315 A1 | 12/2004 | Dell |
| 2005/0002981 A1 | 1/2005 | Lahtinen |
| 2005/0021085 A1 | 1/2005 | Abrams |
| 2005/0059996 A1 | 3/2005 | Bauman |
| 2005/0059997 A1 | 3/2005 | Bauman |
| 2005/0070929 A1 | 3/2005 | Dalessandro |
| 2005/0118435 A1 | 6/2005 | DeLucia |
| 2005/0149073 A1 | 7/2005 | Arani |
| 2006/0004407 A1 | 1/2006 | Hiles |
| 2006/0085030 A1 | 4/2006 | Bettuchi et al. |
| 2006/0135992 A1 | 6/2006 | Bettuchi |
| 2006/0173470 A1 | 8/2006 | Oray |
| 2006/0178683 A1 | 8/2006 | Shimoji |
| 2006/0271104 A1 | 11/2006 | Viola |
| 2007/0026031 A1 | 2/2007 | Bauman |

(56) References Cited

U.S. PATENT DOCUMENTS

| | | |
|---|---|---|
| 2007/0034669 A1 | 2/2007 | de la Torre |
| 2007/0049953 A2 | 3/2007 | Shimoji |
| 2007/0123839 A1 | 5/2007 | Rousseau |
| 2007/0179528 A1 | 8/2007 | Soltz |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia |
| 2008/0009811 A1 | 1/2008 | Cantor |
| 2008/0029570 A1 | 2/2008 | Shelton |
| 2008/0082126 A1 | 4/2008 | Murray |
| 2008/0110959 A1 | 5/2008 | Orban |
| 2008/0125812 A1 | 5/2008 | Zubik |
| 2008/0140115 A1 | 6/2008 | Stopek |
| 2008/0161831 A1 | 7/2008 | Bauman |
| 2008/0161832 A1 | 7/2008 | Bauman |
| 2008/0169327 A1 | 7/2008 | Shelton |
| 2008/0169328 A1 | 7/2008 | Shelton |
| 2008/0169329 A1 | 7/2008 | Shelton |
| 2008/0169330 A1 | 7/2008 | Shelton |
| 2008/0169331 A1 | 7/2008 | Shelton |
| 2008/0169332 A1 | 7/2008 | Shelton |
| 2008/0169333 A1 | 7/2008 | Shelton |
| 2008/0200949 A1 | 8/2008 | Hiles |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi |
| 2008/0308608 A1 | 12/2008 | Prommersberger |
| 2008/0314960 A1 | 12/2008 | Marczyk |
| 2009/0001121 A1 | 1/2009 | Hess |
| 2009/0001122 A1 | 1/2009 | Prommersberger |
| 2009/0001123 A1 | 1/2009 | Morgan |
| 2009/0001124 A1 | 1/2009 | Hess |
| 2009/0001125 A1 | 1/2009 | Hess |
| 2009/0001126 A1 | 1/2009 | Hess |
| 2009/0001128 A1 | 1/2009 | Weisenburgh, II |
| 2009/0001130 A1 | 1/2009 | Hess |
| 2009/0005808 A1 | 1/2009 | Hess |
| 2009/0030452 A1 | 1/2009 | Bauman |
| 2009/0043334 A1 | 2/2009 | Bauman |
| 2009/0076510 A1 | 3/2009 | Bell |
| 2009/0076528 A1 | 3/2009 | Sgro |
| 2009/0078739 A1 | 3/2009 | Viola |
| 2009/0095791 A1 | 4/2009 | Eskaros |
| 2009/0095792 A1 | 4/2009 | Bettuchi |
| 2009/0120994 A1 | 5/2009 | Murray |
| 2009/0134200 A1 | 5/2009 | Tarinelli |
| 2009/0206125 A1 | 8/2009 | Huitema |
| 2009/0206126 A1 | 8/2009 | Huitema |
| 2009/0206139 A1 | 8/2009 | Hall |
| 2009/0206141 A1 | 8/2009 | Huitema |
| 2009/0206142 A1 | 8/2009 | Huitema |
| 2009/0206143 A1 | 8/2009 | Huitema |
| 2009/0218384 A1 | 9/2009 | Aranyi |
| 2009/0277944 A9 | 11/2009 | Dalessandro et al. |
| 2009/0277947 A1 | 11/2009 | Viola |
| 2009/0287230 A1 | 11/2009 | D'Agostino |
| 2010/0012704 A1 | 1/2010 | Tarinelli Racenet |
| 2010/0065606 A1 | 3/2010 | Stopek |
| 2010/0065607 A1 | 3/2010 | Orban, III |
| 2010/0072254 A1 | 3/2010 | Aranyi |
| 2010/0147921 A1 | 6/2010 | Olson |
| 2010/0147922 A1 | 6/2010 | Olson |
| 2010/0147923 A1 | 6/2010 | D'Agostino |
| 2010/0243707 A1 | 9/2010 | Olson |
| 2010/0243708 A1 | 9/2010 | Aranyi |
| 2010/0243711 A1 | 9/2010 | Olson |
| 2010/0249805 A1 | 9/2010 | Olson |
| 2010/0264195 A1 | 10/2010 | Bettuchi |
| 2010/0282815 A1 | 11/2010 | Bettuchi |
| 2010/0331880 A1 | 12/2010 | Stopek |
| 2011/0024476 A1 | 2/2011 | Bettuchi |
| 2011/0024481 A1 | 2/2011 | Bettuchi |
| 2011/0036894 A1 | 2/2011 | Bettuchi |
| 2011/0042442 A1 | 2/2011 | Viola |
| 2011/0046650 A1 | 2/2011 | Bettuchi |
| 2011/0057016 A1 | 3/2011 | Bettuchi |
| 2011/0087279 A1 | 4/2011 | Shah |
| 2011/0095070 A1* | 4/2011 | Patel ............ A61B 17/115 227/181.1 |
| 2011/0215132 A1 | 9/2011 | Aranyi |
| 2012/0061447 A1* | 3/2012 | Williams ......... A61B 17/115 227/175.1 |
| 2012/0074199 A1 | 3/2012 | Olson |
| 2012/0080336 A1 | 4/2012 | Shelton |
| 2012/0083723 A1 | 4/2012 | Vitaris et al. |
| 2012/0187179 A1 | 7/2012 | Gleiman |
| 2012/0197272 A1 | 8/2012 | Oray et al. |
| 2012/0241499 A1 | 9/2012 | Baxter |
| 2012/0273547 A1 | 11/2012 | Hodgkinson |
| 2013/0037596 A1 | 2/2013 | Bear |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0181035 A1* | 7/2013 | Milliman ........ A61B 17/1155 227/180.1 |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0256380 A1 | 10/2013 | Schmid et al. |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1* | 8/2014 | Milliman ........ A61B 17/07292 227/179.1 |
| 2014/0217148 A1* | 8/2014 | Penna ............ A61B 17/07292 227/179.1 |
| 2014/0239046 A1 | 8/2014 | Milliman |
| 2014/0239047 A1 | 8/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |

(56) References Cited

U.S. PATENT DOCUMENTS

| | | |
|---|---|---|
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0305743 A1 | 10/2015 | Casasanta et al. |
| 2015/0327864 A1 | 11/2015 | Hodgkinson et al. |
| 2015/0351758 A1* | 12/2015 | Shelton, IV ..... A61B 17/00491 606/219 |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |

FOREIGN PATENT DOCUMENTS

| | | |
|---|---|---|
| CN | 101332110 A | 12/2008 |
| DE | 1 99 24 311 | 11/2000 |
| EP | 0 594 148 | 4/1994 |
| EP | 0 327 022 | 4/1995 |
| EP | 0 667 119 | 8/1995 |
| EP | 1 064 883 | 1/2001 |
| EP | 1 256 317 | 11/2002 |
| EP | 1 256 318 | 11/2002 |
| EP | 1 520 525 | 4/2005 |
| EP | 1 621 141 | 2/2006 |
| EP | 1 702 570 | 9/2006 |
| EP | 1 759 640 | 3/2007 |
| EP | 1 815 804 | 8/2007 |
| EP | 1 825 820 | 8/2007 |
| EP | 1 929 958 | 6/2008 |
| EP | 1 994 890 | 11/2008 |
| EP | 2 005 894 | 12/2008 |
| EP | 2 005 895 | 12/2008 |
| EP | 2 008 595 | 12/2008 |
| EP | 2 039 308 A2 | 3/2009 |
| EP | 2 090 231 | 8/2009 |
| EP | 2 090 244 | 8/2009 |
| EP | 2 090 252 | 8/2009 |
| EP | 2 163 211 A2 | 3/2010 |
| EP | 2 189 121 A1 | 5/2010 |
| EP | 2 198 787 | 6/2010 |
| EP | 2 236 098 | 10/2010 |
| EP | 2 236 099 | 10/2010 |
| EP | 2 258 282 A2 | 12/2010 |
| EP | 2 292 276 A2 | 3/2011 |
| EP | 2 311 386 | 4/2011 |
| EP | 2 436 348 | 4/2012 |
| EP | 2 462 880 | 6/2012 |
| EP | 2 497 431 A1 | 9/2012 |
| EP | 2 517 637 | 10/2012 |
| EP | 2 586 380 | 5/2013 |
| EP | 2604195 | 6/2013 |
| EP | 2604197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 762 091 A2 | 8/2014 |
| JP | 2000-166933 | 6/2000 |
| JP | 2002-202213 | 7/2002 |
| JP | 2007-124166 | 5/2007 |
| WO | WO 90/05489 | 5/1990 |
| WO | WO 95/16221 | 6/1995 |
| WO | WO 96/22055 | 7/1996 |
| WO | WO 97/01989 | 1/1997 |
| WO | WO 97/13463 | 4/1997 |
| WO | WO 98/17180 | 4/1998 |
| WO | 98/38923 A1 | 9/1998 |
| WO | WO 99/45849 | 9/1999 |
| WO | WO 03/082126 | 10/2003 |
| WO | WO 03/088845 | 10/2003 |
| WO | WO 03/094743 | 11/2003 |
| WO | WO 03/105698 | 12/2003 |
| WO | WO 2005/079675 | 9/2005 |
| WO | WO 2006/023578 | 3/2006 |
| WO | WO 2006/044490 | 4/2006 |
| WO | WO 2006/083748 | 8/2006 |
| WO | WO 2007/121579 | 11/2007 |
| WO | WO 2008/057281 | 5/2008 |
| WO | WO 2008/109125 | 9/2008 |
| WO | WO 2010/075298 | 7/2010 |
| WO | WO 2011/143183 | 11/2011 |
| WO | WO 2012/044848 | 4/2012 |

OTHER PUBLICATIONS

Extended European Search Report corresponding to EP 14 16 9739.1, completed Aug. 19, 2014 and Aug. 29, 2014; (7 pp).

Extended European Search Report corresponding to EP 14 15 7997.9, completed Sep. 9, 2014 and mailed Sep. 17, 2014; (8 pp).

Extended European Search Report corresponding to EP 14 16 8904.2, completed Sep. 10, 2014 and mailed Sep. 18, 2014; (8 pp).

Extended European Search Report corresponding to EP 13 19 4995.0, completed Jun. 5, 2014 and mailed Oct. 13, 2014; (10 pp).

Extended European Search Report corresponding to EP 13 15 4571.7, completed Oct. 10, 2014 and mailed Oct. 20, 2014; (8 pp).

Extended European Search Report corresponding to EP 14 18 1125.7, completed Oct. 16, 2014 and mailed Oct. 24, 2014; (7 pp).

Extended European Search Report corresponding to EP 14 18 1127.3, completed Oct. 16, 2014 and mailed Nov. 10, 2014; (8 pp).

Extended European Search Report corresponding to EP 14 19 0419.3, completed Mar. 24, 2015 and mailed Mar. 30, 2015; (6 pp).

Extended European Search Report corresponding to EP 13 19 2123.1, completed Jan. 30, 2014 and mailed Feb. 10, 2014; (8 pp).

Extended European Search Report corresponding to EP 13 19 2111.6, completed Feb. 13, 2014 and mailed Feb. 27, 2014; (10 pp).

Extended European Search Report corresponding to EP 13 19 5919.9, completed Feb. 10, 2014 and mailed Mar. 3, 2014; (7 pp).

Extended European Search Report corresponding to EP 08 72 6500.5, completed Feb. 20, 2014 and mailed Mar. 3, 2014; (7 pp).

Extended European Search Report corresponding to EP 13 19 5019.8, completed Mar. 14, 2014 and mailed Mar. 24, 2014; (7 pp).

Extended European Search Report corresponding to EP 13 19 6816.6, completed Mar. 28, 2014 and mailed Apr. 9, 2014; (9 pp).

Extended European Search Report corresponding to EP 13 19 7958.5, completed Apr. 4, 2014 and mailed Apr. 15, 2014; (8 pp).

Extended European Search Report corresponding to EP 13 19 4995.0, completed Jun. 5, 2014 and mailed Jun. 16, 2014; (5 pp).

Extended European Search Report corresponding to EP 14 15 7195.0, completed Jun. 5, 2014 and mailed Jun. 18, 2014; (9 pp).

European Search Report corresponding to EP 05 02 2585.3, completed Jan. 25, 2006 and mailed Feb. 3, 2006; (4 pp).

European Search Report corresponding to EP 06 00 4598, completed Jun. 22, 2006; (2 pp).

European Search Report corresponding to EP 06 01 6962.0, completed Jan. 3, 2007 and mailed Jan. 11, 2007; (10 pp).

International Search Report corresponding to International Application No. PCT/US2005/036740, completed Feb. 20, 2007 and mailed Mar. 23, 2007; (8 pp).

International Search Report corresponding to International Application No. PCT/US2007/022713, completed Apr. 21, 2008 and mailed May 15, 2008; (1 p).

International Search Report corresponding to International Application No. PCT/US2008/002981, completed Jun. 9, 2008 and mailed Jun. 26, 2008; (2 pp).

European Search Report corresponding to EP 08 25 1779, completed Jul. 14, 2008 and mailed Jul. 23, 2008; (5 pp).

European Search Report corresponding to EP 08 25 1989.3, completed Mar. 11, 2010 and mailed Mar. 24, 2010; (6 pp).

(56) References Cited

OTHER PUBLICATIONS

European Search Report corresponding to EP 10 25 0639.1, completed Jun. 17, 2010 and mailed Jun. 28, 2010; (7 pp).
European Search Report corresponding to EP 10 25 0715.9, completed Jun. 30, 2010 and mailed Jul. 20, 2010; (3 pp).
European Search Report corresponding to EP 05 80 4382.9, completed Oct. 5, 2010 and mailed Oct. 12, 2010; (3 pp).
European Search Report corresponding to EP 10 25 1437.9, completed Nov. 22, 2010 and mailed Dec. 16, 2010; (3 pp).
European Search Report corresponding to EP 09 25 2897.5, completed Feb. 7, 2011 and mailed Feb. 15, 2011; (3 pp).
European Search Report corresponding to EP 10 25 0642.5, completed Mar. 25, 2011 and mailed Apr. 4, 2011; (4 pp).
European Search Report corresponding to EP 11 18 8309.6, completed Dec. 15, 2011 and mailed Jan. 12, 2012; (3 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and mailed May 3, 2012; (10 pp).
European Search Report corresponding to EP 12 16 5609.4, completed Jul. 5, 2012 and mailed Jul. 13, 2012; (8 pp).
European Search Report corresponding to EP 12 15 8861.0, completed Jul. 17, 2012 and mailed Jul. 24, 2012; (9 pp).
European Search Report corresponding to EP 12 16 5878.5, completed Jul. 24, 2012 and mailed Aug. 6, 2012; (8 pp).
Extended European Search Report corresponding to EP 12 19 1035.0, completed Jan. 11, 2013 and mailed Jan. 18, 2013; (7 pp).
Extended European Search Report corresponding to EP 12 18 6175.1, completed Jan. 15, 2013 and mailed Jan. 23, 2013; (7 pp).
Extended European Search Report corresponding to EP 12 19 1114.3, completed Jan. 23, 2013 and mailed Jan. 31, 2013; (10 pp).
Extended European Search Report corresponding to EP 12 19 2224.9, completed Mar. 14, 2013 and mailed Mar. 26, 2013; (8 pp).
Extended European Search Report corresponding to EP 12 19 6904.2, completed Mar. 28, 2013 and mailed Jul. 26, 2013; (8 pp).
Extended European Search Report corresponding to EP 12 19 6911.7, completed Apr. 18, 2013 and mailed Apr. 24, 2013; (8 pp).
Extended European Search Report corresponding to EP 07 00 5842.5, completed May 13, 2013 and mailed May 29, 2013; (7 pp).
Extended European Search Report corresponding to EP 12 19 8776.2, completed May 16, 2013 and mailed May 27, 2013; (8 pp).
Extended European Search Report corresponding to EP 12 19 8749.9, completed May 21, 2013 and mailed May 31, 2013; (8 pp).
Extended European Search Report corresponding to EP 13 15 6297.7, completed Jun. 4, 2013 and mailed Jun. 13, 20131; (7 pp).
Extended European Search Report corresponding to EP 13 17 3985.6, completed Aug. 19, 2013 and mailed Aug. 28, 2013; (6 pp).
Extended European Search Report corresponding to EP 13 17 3986.4, completed Aug. 20, 2013 and mailed Aug. 29, 2013; (6 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 14 15 6342.9, completed Jul. 22, 2014 and mailed Jul. 29, 2014; (8 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Chinese Notification of Reexamination corresponding to counterpart Int'l Appln. No. CN 201010517292.8 dated Jun. 2, 2015.
Extended European Search Report corresponding to counterpart Int'l Appln. No. EP 14 15 2060.1 dated Aug. 14, 2015.
Japanese Office Action corresponding to counterpart Int'l Appln. No. JP 2014-216989 mailed Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 mailed Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 mailed Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.

(56) References Cited

OTHER PUBLICATIONS

Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 mailed May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.

\* cited by examiner

CIRCULAR STAPLING DEVICE WITH BUTTRESS

CROSS-REFERENCE TO RELATED APPLICATIONS

This application claims the benefit of and priority to U.S. Provisional Patent Application No. 61/768,661, filed Feb. 25, 2013, the entire disclosure of which is incorporated by reference herein.

TECHNICAL FIELD

The present disclosure relates to surgical stapling devices and, more particularly, to structures and methods for removably attaching buttress material to circular surgical stapling devices for use in anastomosis procedures.

BACKGROUND

Fasteners have traditionally been used to replace suturing when joining various body structures such as, for example, the bowel or bronchus. Surgical stapling devices employed to apply these fasteners are generally designed to simultaneously cut and seal tissue to reduce the time and risks involved with anastomosis procedures.

Circular surgical stapling devices are employed by surgeons to sequentially or simultaneously apply one or more surgical fasteners, e.g., staples or two-part fasteners, to body tissue for the purpose of joining segments of body tissue together and/or for the creation of anastomoses. Circular surgical stapling devices generally include an annular fastener cartridge assembly that supports a plurality of annular rows of fasteners, an annular anvil assembly operatively associated with the fastener cartridge assembly which provides a surface against which the fasteners are formed upon a firing of the circular stapling device, and an annular blade for cutting tissue.

For most procedures, the use of bare fasteners, with the fasteners in direct contact with the patient's tissue, is generally acceptable. The integrity of the tissue will normally serve to prevent the fasteners from tearing out of the tissue and compromising the sealing before healing has occurred. However, in some surgical operations buttress materials are employed by surgeons in combination with circular stapling devices to bridge, repair and/or reinforce tissue defects within a patient. In particular, buttress materials reduce the trauma suffered by the patient, reduce the instances of leakage, reduce the instances of bleeding, and create a relatively strong bond between adjacent body tissues.

Accordingly, there is a need for reliably and removably attaching buttress material onto a circular stapling device so that the buttress material does not interfere with the operation of the device, remains on the device until after the fasteners are fired, and is convenient and easy to install and use.

SUMMARY

According to one aspect, a circular stapling device includes a handle assembly, an elongate body that extends from the handle assembly, a cartridge assembly mounted on a distal end of the elongate body, a circular cartridge buttress member, a retaining ring member, and a knife assembly.

The cartridge assembly defines an annular containment groove and includes a housing, a pusher member, and a fastener cartridge body. In embodiments, the housing and the fastener cartridge body together define the containment groove therebetween. The pusher member is supported within the housing and is movable between a first position and a second position. The fastener cartridge body is supported on the housing and has a tissue engaging surface that extends to an annular edge.

The circular cartridge buttress member has a body portion and an extension portion. The body portion is supported on the tissue engaging surface of the fastener cartridge body. The extension portion extends from the body portion and over the annular edge of the tissue engaging surface.

The retaining ring member is secured within the containment groove over the extension portion of the circular cartridge buttress member to releasably secure the circular cartridge buttress member to the fastener cartridge body. In embodiments, the retaining ring member is an o-ring. The o-ring is formed of an elastomeric material.

The knife assembly includes a primary knife blade and a secondary knife blade. The primary knife blade is dimensioned to cut tissue. The secondary knife blade is connected to the pusher member. The secondary knife blade is movable with the pusher member to cut the retaining ring member and relieve a tension that the retaining ring member exerts on the extension portion of the circular cartridge buttress member. The tension is sufficient to maintain the circular cartridge buttress member secured to the fastener cartridge body.

The fastener cartridge body supports a stop member that defines a receiving channel dimensioned to receive the retaining ring member and a knife slot dimensioned to receive a distal end portion of the secondary knife blade. The stop member includes a cross member dimensioned to prevent tissue from extruding in front of the distal end portion of the secondary knife blade. The distal end portion of the secondary knife blade is engageable with the cross member upon a translation of the distal end portion of the secondary knife blade through the knife slot. In embodiments, the stop member is formed of a polyethylene material.

The housing includes one or more containment tabs that extends distally from a distal end portion of the housing so that an inner surface of the one or more containment tabs are engageable with an outer surface of the retaining ring member to maintain the retaining ring member secured to the housing after the retaining ring member is cut with the secondary knife blade.

In accordance with another aspect, a cartridge assembly includes a housing, a pusher member, a fastener cartridge body, a circular cartridge buttress member, and a retaining ring member. The cartridge assembly further includes a tissue cutting knife blade dimensioned to cut tissue.

The pusher member is supported within the housing and is movable between a first position and a second position.

The fastener cartridge body is supported on the housing and has a tissue engaging surface that extends to an annular edge. One or both of the housing and the fastener cartridge body define an annular containment groove.

The circular cartridge buttress member has a body portion and an extension portion. The body portion is supported on the tissue engaging surface of the fastener cartridge body. The extension portion extends from the body portion and over the annular edge of the tissue engaging surface.

The retaining ring member is secured within the containment groove to releasably secure the extension portion of the circular cartridge buttress member to the cartridge assembly. In embodiments, the retaining ring member is an o-ring formed of elastomeric material.

A knife blade is connected to the pusher member. The knife blade is movable with the pusher member to cut the retaining ring member and relieve a tension that the retaining ring member exerts on the extension portion of the circular cartridge buttress member. The tension is sufficient to maintain the circular cartridge buttress member secured to the fastener cartridge body.

The fastener cartridge body supports a stop member that defines a receiving channel dimensioned to receive the retaining ring member and a knife slot dimensioned to receive a distal end portion of the knife blade. The stop member includes a cross member dimensioned to prevent tissue from extruding in front of the distal end portion of the knife blade. The distal end portion of the knife blade is engageable with the cross member upon a translation of the distal end portion of the knife blade through the knife slot. In embodiments, the stop member is formed of a polyethylene material.

The housing includes one or more containment tabs that extend distally from a distal end portion of the housing so that an inner surface of the one or more containment tabs are engageable with an outer surface of the retaining ring member to maintain the retaining ring member secured to the housing.

According to yet another aspect, the present disclosure is directed to a method for releasing a cartridge buttress member from a cartridge assembly of a circular stapling device. The method involves providing a circular stapling device including an elongate member having a cartridge assembly mounted on a distal end of the elongate body. The cartridge assembly defines a containment groove and includes a retaining ring member and a cartridge buttress member. The cartridge buttress member has a body portion and an extension portion. The retaining ring member is disposed within the containment groove over the extension portion to secure the body portion on a tissue engaging surface of the cartridge assembly. The method includes cutting the retaining ring member to release the cartridge buttress member from the circular stapling device.

When the circular stapling device includes a knife blade secured to a pusher member supported within the cartridge assembly, the method involves the step of moving the knife blade by moving the pusher member such that the knife blade cuts the retaining ring member. One step includes preventing tissue from extruding in front of the knife blade. One step involves relieving a tension that the retaining ring member exerts on the extension portion of the circular cartridge buttress member. The method includes cutting tissue with another knife blade.

Other aspects, features, and advantages will be apparent from the description, drawings, and claims.

BRIEF DESCRIPTION OF DRAWINGS

The accompanying drawings, which are incorporated in and constitute a part of this specification, illustrate embodiments of the disclosure and, together with a general description of the disclosure given above and the detailed description given below, serve to explain the principles of the disclosure, wherein.

DETAILED DESCRIPTION

Figure 1:
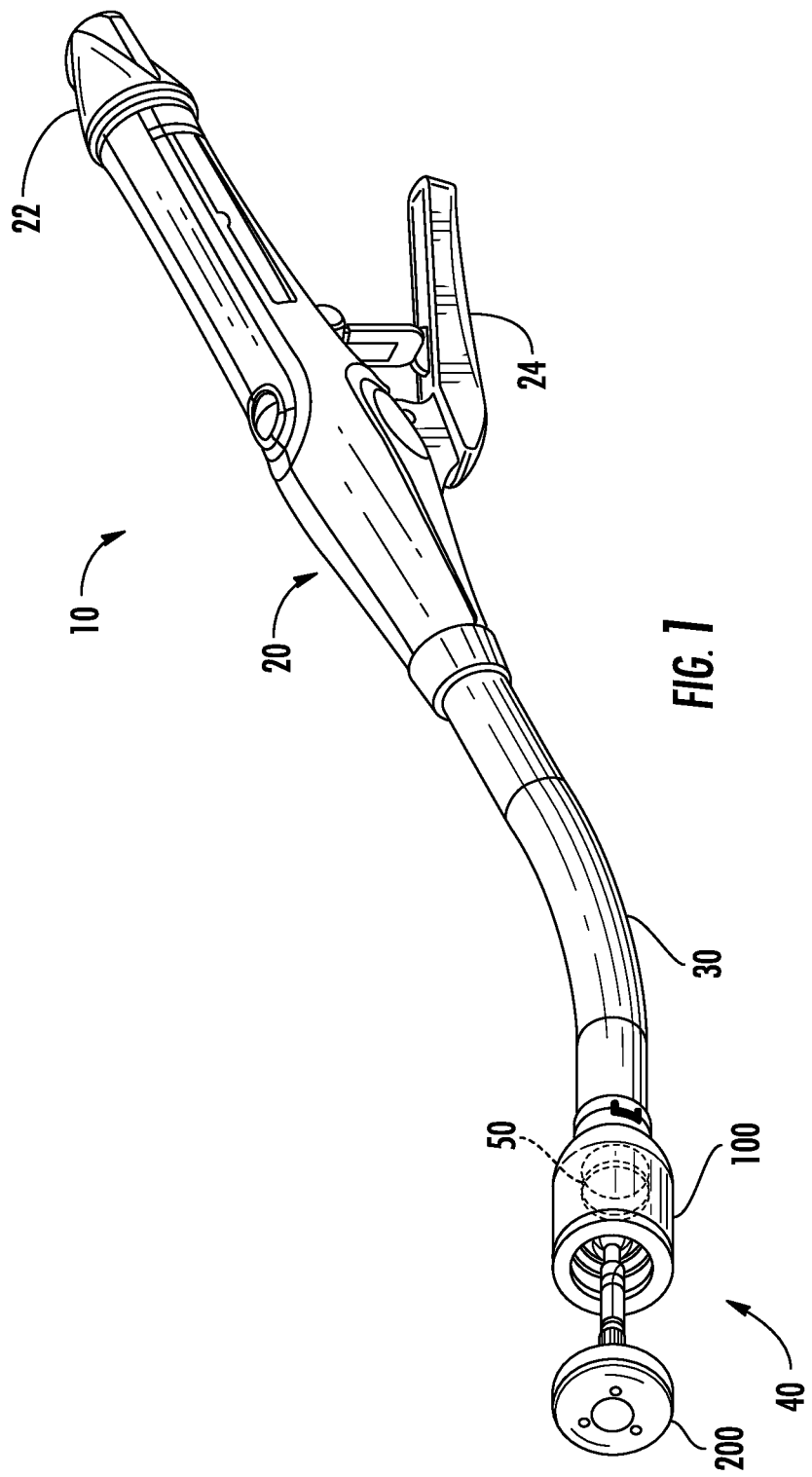
FIG. 1 is a perspective view of a circular surgical stapling device according to the present disclosure.

As used herein, the term "clinician" refers to a doctor, a nurse, or any other care provider and may include support personnel. Particular embodiments of the present disclosure will be described herein with reference to the accompanying drawings. As shown in the drawings and as described throughout the following description, and as is traditional when referring to relative positioning on an object, the term "proximal" refers to the end of the device that is closer to the clinician and the term "distal" refers to the end of the device that is farther from the clinician. In the following description, well-known functions or constructions are not described in detail to avoid obscuring the present disclosure in unnecessary detail.

Referring initially to FIG. 1, a circular surgical stapling device for use with a buttress material is disclosed herein and is generally designated as 10. In embodiments, the surgical stapling device 10 is adapted for reuse and in certain embodiments; the surgical stapling device 10 is adapted for a single use and can be disposable.

Reference may be made to U.S. Pat. No. 5,915,616 to Viola et al. and commonly owned U.S. Patent Application Publication No. 2011/0174099, filed on Nov. 15, 2010, entitled "Adapters for Use Between Surgical Handle Assembly and Surgical End Effector," the entire contents of which are incorporated herein by reference, for a detailed discussion of the construction and operation of exemplary circular stapling devices.

The surgical stapling device 10 includes a handle assembly 20, a tubular elongate body 30, an end effector 40, and a knife assembly 50. The handle assembly 20 includes a rotatable advancing member 22 and a pivotable trigger member 24 that are operatively coupled to one or more drivers supported by the surgical stapling device 10. The elongate body 30 extends distally from a distal end portion of the handle assembly 20 to a proximal end portion of the end effector 40 so that the elongate body 30 is disposed between the handle assembly 20 and the end effector 40. In some embodiments, the elongate body 30 has a linear shape along the length of the elongate body 30, and in certain embodiments, the elongate body 30 has a curved shape along the length of the elongate body 30.

The end effector 40 includes a fastener cartridge assembly 100 and an anvil assembly 200. Notably, the fastener cartridge assembly 100 and/or the anvil assembly 200 may be replaced and the circular stapling device 10 may be reused.

Figure 5A:
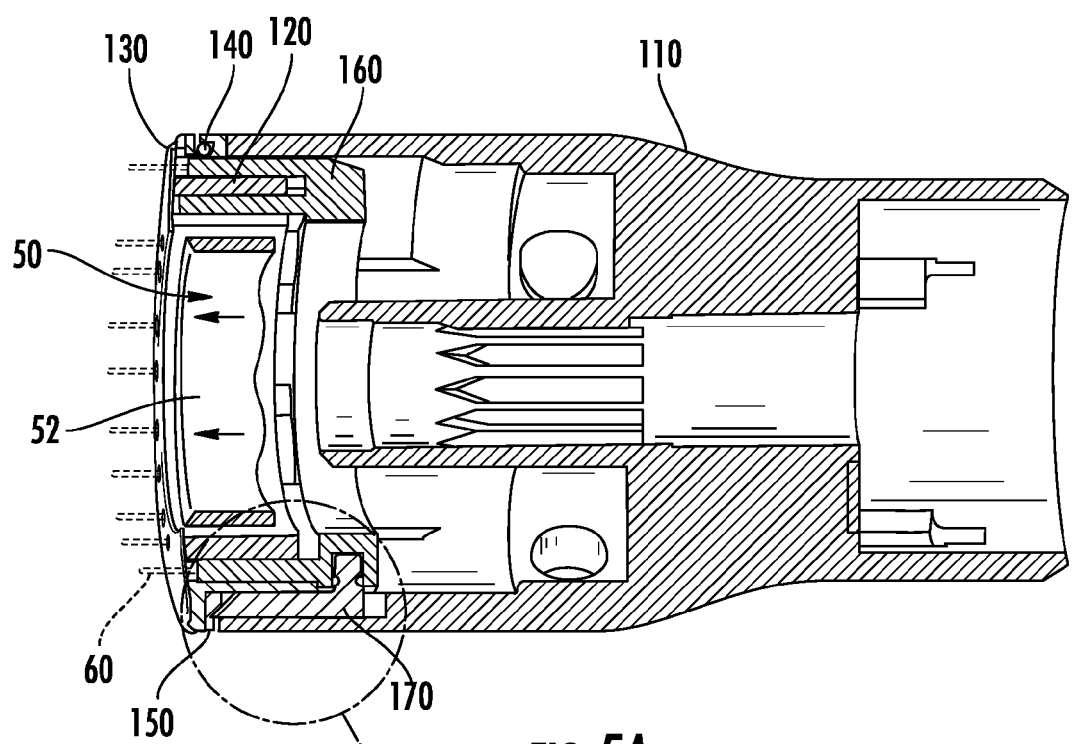
FIG. 5A is an enlarged, longitudinal, cross-sectional view of the cartridge assembly of FIGS. 2 and 3A shown in a second configuration with a distal portion of a knife of the presently disclosed circular surgical stapling device shown being distally advanced through the cartridge assembly.

With reference to FIG. 5A, the knife assembly 50 is supported within the end effector 40 and includes a substantially cylindrical knife blade 52 adapted to sever tissue and a secondary knife blade 170 adapted to severe a retaining ring member 140 that secures a cartridge buttress member 130 to a cartridge body 120 of the cartridge assembly 100, as will be described in greater detail below. In embodiments, the retaining ring member 140 is an o-ring, a tie, a band, or a suture. In embodiments, the retaining ring member 140 is formed of an elastomeric material.

The circular stapling device 10 can include any number of drivers to effectuate a firing of the stapling device 10 including, for example, a first driver that is operable to effectuate the firing and formation of fasteners 60 (see FIGS. 4 and 5) supported by the end effector 40 and/or the severance of the retaining ring member 140, and second driver that is operable to advance the cylindrical knife blade 52 separate and/or independent of the first driver. Alternatively, a single driver may be used to fire and form the fasteners 60, and to advance one or both the cylindrical knife blade 52 and the secondary knife blade 170.

Turning now to FIGS. 2-5B, the fastener cartridge assembly 100 is mounted on a distal end portion of the elongate body 30. The fastener cartridge assembly 100 includes a housing 110, a fastener cartridge body 120, a circular cartridge buttress member 130, a retaining ring member 140, a stop member 150, a pusher member 160, and a secondary knife blade 170.

With reference to FIG. 3A, the housing 110 includes a shell body 112 having a plurality of fingers 114 extending around a distal end portion of the shell body 112. At least some of the plurality of fingers 114 define an opening 114a therethrough, and at least some of the plurality of fingers include a containment tab 114b that extends distally from a distal end portion of the respective fingers 114. The containment tabs 114b are dimensioned to maintain the retaining ring member 140 secured to the housing 110 after the retaining ring member 140 is cut by the secondary knife blade 170, as described in greater detail below.

Figure 4:
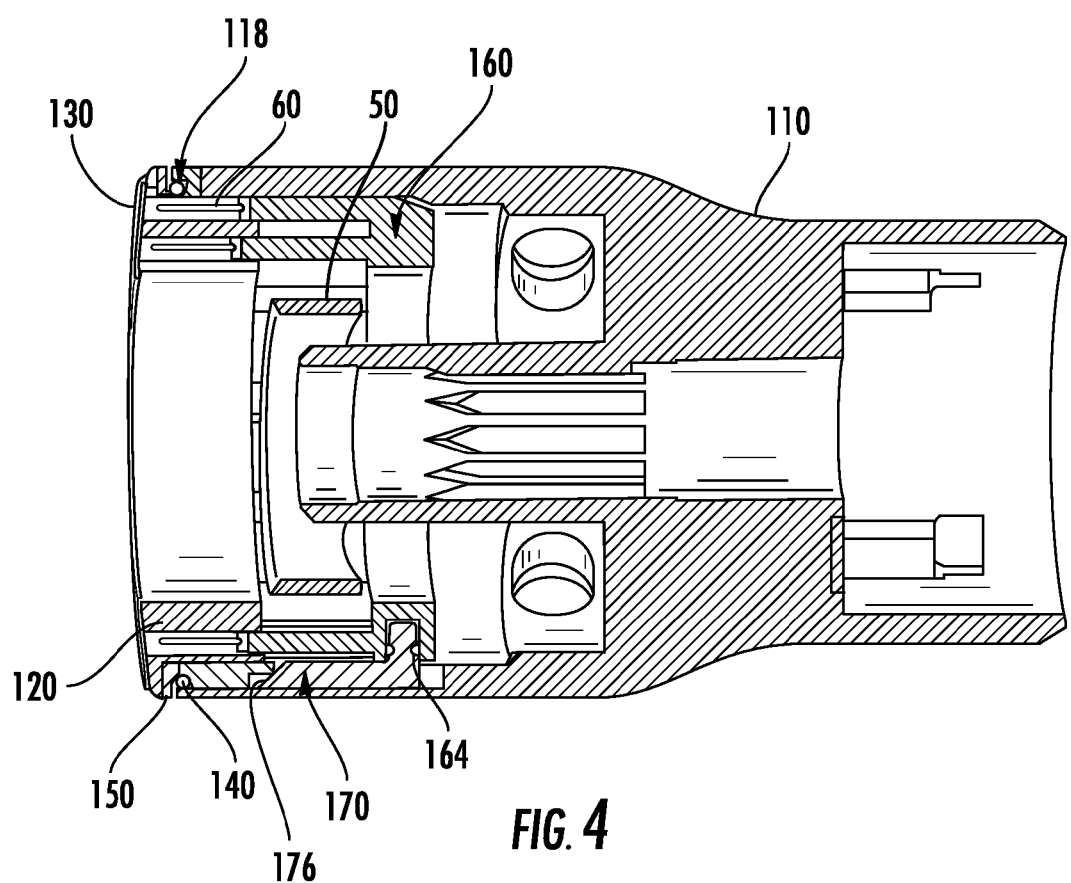
FIG. 4 is an enlarged, longitudinal, cross-sectional view of the cartridge assembly of FIGS. 2 and 3A shown in a first configuration.
Figure 5B:
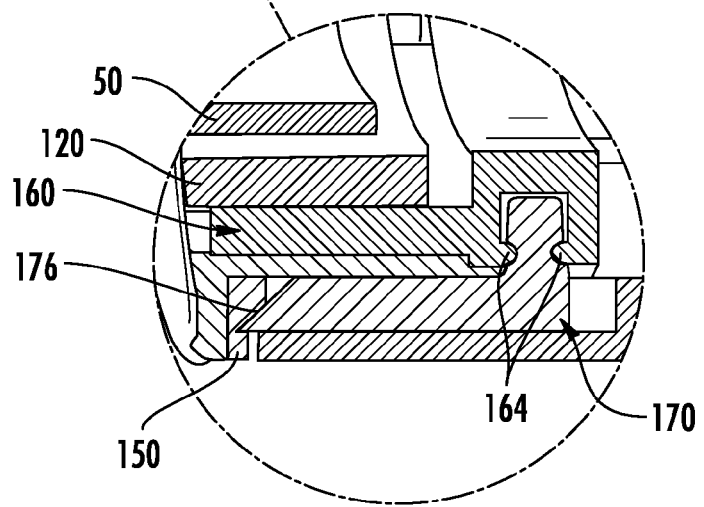
FIG. 5B is an enlarged view of the indicated area of detail shown in FIG. 5A.

With reference to FIG. 4, a radial or annular containment groove 118 is defined between a proximal surface of the fastener cartridge body 120 and a distal end portion of the shell body 112 such that the housing 110 and the fastener cartridge body 120 together define the annular containment groove 118 therebetween. The containment groove 118 extends radially along an inner surface of each containment tab 114b and is dimensioned to receive the retaining ring member 140.

The containment groove 118 is defined by a chamfer extending radially around the periphery of a distal-most rim or edge of the shell body 112. Each finger 114 is defined by a pair of longitudinally extending elongate slots 116 that are defined in a distal end portion of the shell body 112.

The distal end portion of the housing 110 is dimensioned to receive the cartridge body 120 therein.

The cartridge body 120 is supported on the housing 110 and includes a tissue engaging surface 122 that extends to an annular edge 122a and defines a plurality of fastener retaining slots 124 in an annular and/or concentric array about the tissue engaging surface 122. Each fastener retaining slot 124 is dimensioned to support a fastener 60 (FIG. 4) such as a surgical staple. The cartridge body 120 includes a sidewall 126 having a plurality of radially spaced detents 126a extending radially outward from an outer surface of the sidewall 126. Each detent 126a is dimensioned to be received within one of the plurality of openings 114a defined in the fingers 114 of the housing 110 to secure the cartridge body 120 to the distal end portion of the housing 110 when the cartridge body 120 is positioned in the distal end portion of the housing 110. A stop member support 128 radially extends from the outer surface of the sidewall 126. Stop member support 128 is dimensioned to secure the stop member 150 to the cartridge body 120.

The cartridge buttress member 130 has a body portion 132 and an extension portion 134 that extends from the body portion 132 of the cartridge buttress member 130. In use, the body portion 132 is supported on the tissue engaging surface 122 of the cartridge body 120. Also in use, the extension portion 134 is dimensioned to extend over the annular edge 122a of the tissue engaging surface 122 of the cartridge body 120 and against an outer surface of the housing 110.

Figure 2:
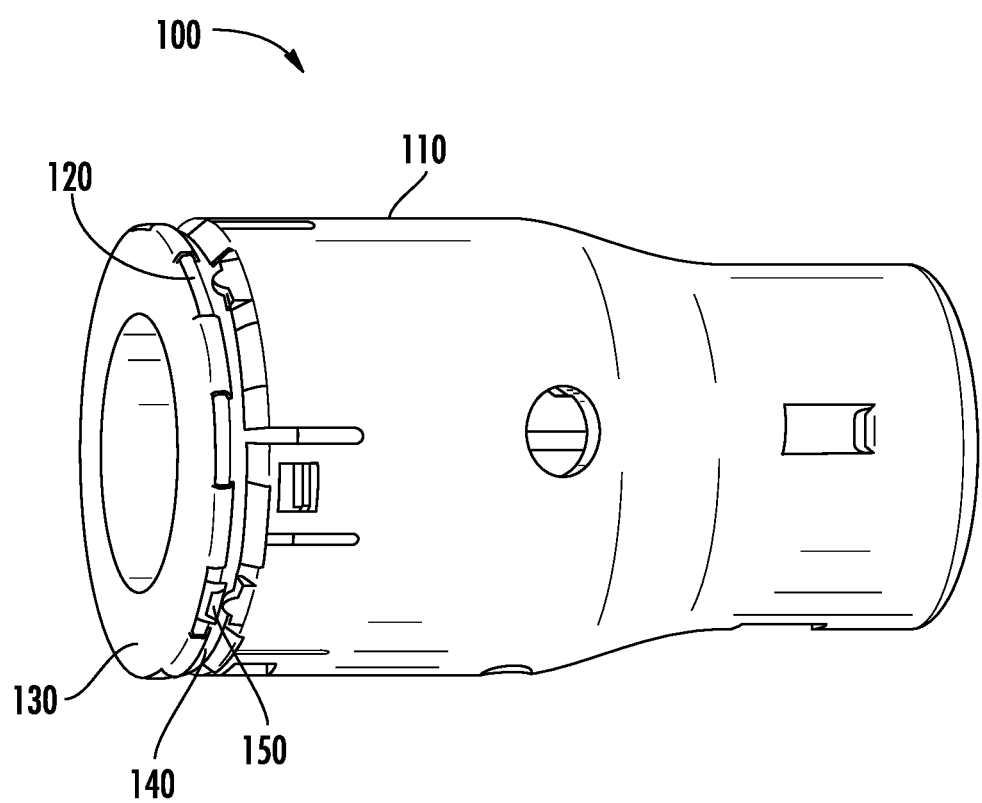
FIG. 2 is an enlarged perspective view of a cartridge assembly of the circular stapling device of FIG. 1.
Figure 3:
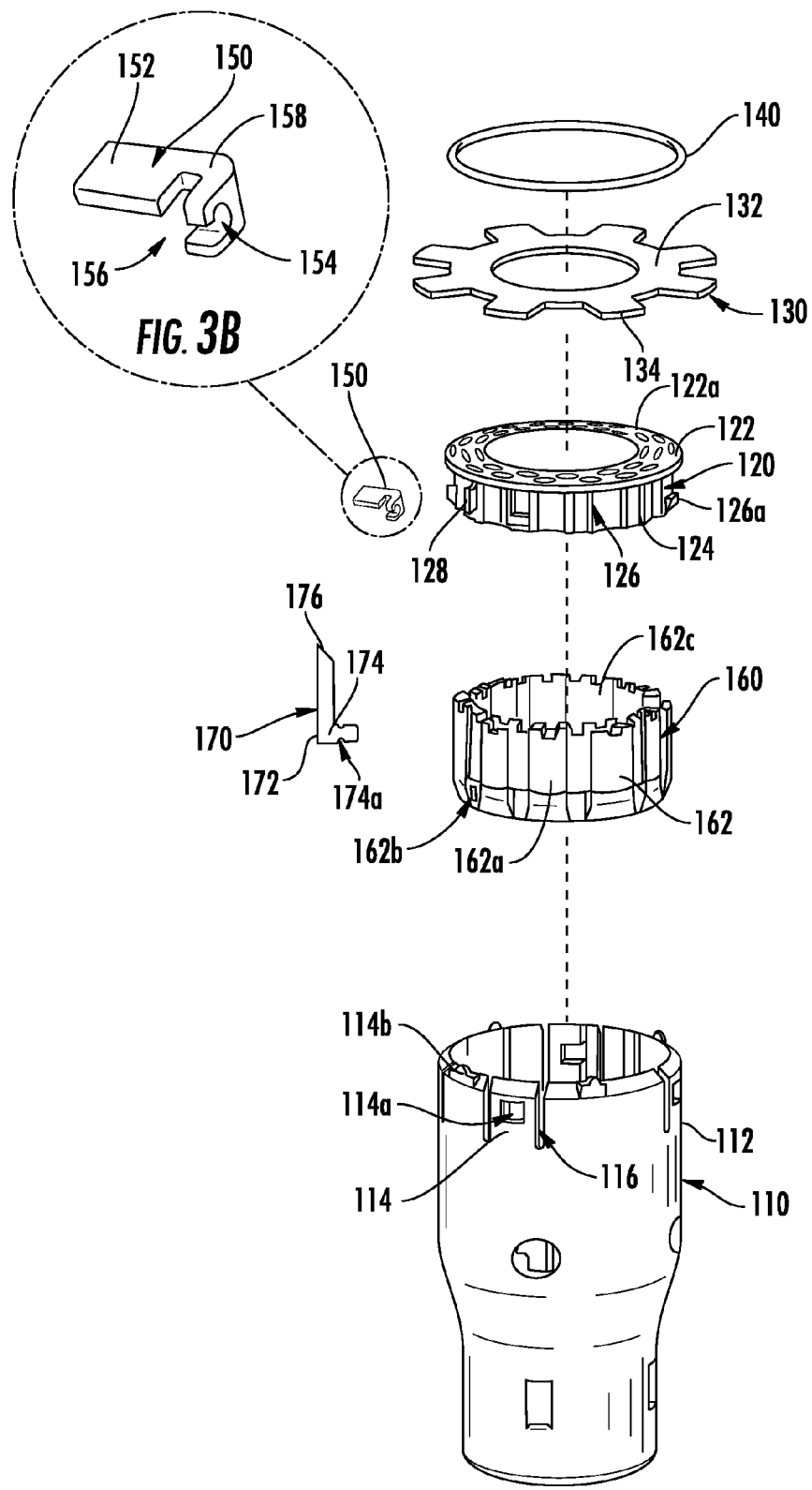
FIG. 3A is a perspective view, with parts separated, of the cartridge assembly shown in FIG. 2.
FIG. 3B is an enlarged perspective view of a stop member of the cartridge assembly of FIGS. 2 and 3A.

As seen in FIG. 2, with extension portion 134 of cartridge buttress member 130 extending against the outer surface of the housing 110, the retaining ring member 140 may be positioned around the outer surface of the extension portion 134, along the inner surface of the containment tabs 114b of the housing 110, and within the radial containment groove 118 to secure the extension portion 134 of the cartridge buttress member 130 to the cartridge assembly 100. In so doing, the retaining ring member 140, together with the containment tabs 114b and the grooves 118 of the housing 110 function to maintain the body portion 132 of the cartridge buttress member 130 against the tissue engaging surface 122 of the cartridge body 120, as illustrated in FIG. 2.

The retaining ring member 140 is secured within the containment groove 118 over the extension portion 134 to releasably secure the circular cartridge buttress member 130 to the fastener cartridge body 120.

The stop member 150 is securable to the cartridge body 120 and is dimensioned to be received by the stop member support 128 of the cartridge body 120. In embodiments, the stop member 150 is formed of a polyethylene material. As seen in FIG. 3B, the stop member 150 includes stop member body 152 that defines a ring receiving channel 154 therethrough. The ring receiving channel 154 is dimensioned to receive the retaining ring member 140 and secure the retaining ring member 140 within the ring receiving channel 154. The stop member body 152 defines a knife slot 156 dimensioned to receive a distal end portion of the secondary knife blade 170 and a cross member 158 dimensioned to limit distal advancement of the secondary knife blade 170 and prevent tissue from extruding in front or distal of the secondary knife blade 170, as will be described in greater detail below. The knife slot 156 is defined in the stop member body 152 in a direction substantially traverse to the ring receiving channel 154.

The pusher member 160 includes a substantially cylindrical body 162 having a plurality of distally extending pushers 162a. The plurality of pushers 162 is disposed in an annular and/or concentric array about the cylindrical body 162 of the pusher member 160. The pusher member 160 defines a knife supporting slot 162b dimensioned to receive a support arm 174 of secondary knife blade 170 to secure the secondary knife blade 170 to the cylindrical body 162 of the pusher member 160. As seen in FIGS. 4 and 5A, a pair of opposed nubs 164 extend from the cylindrical body 162 into the knife supporting slot 162b. An inner surface of the cylindrical body 162 defines a central opening 162c dimensioned to receive the cylindrical knife 52 therethrough (see FIG. 5A).

The pusher member 160 is movably supported within the housing 110 and is operatively coupled to a driver adapted to drive the pusher member 160 through the housing 110 between a proximal position and a distal position to dispense the fasteners 60 retained in the fastener retaining slots 124 of the cartridge body 120 and to distally drive the secondary knife blade 170 to sever the retaining ring member 140 upon a firing of the circular stapling device 10.

The secondary knife blade 170 is connected to the pusher member 160 and movable with the pusher member 160 to cut the retaining ring member 140 and relieve a tension that the retaining ring member 140 exerts on the extension portion 134 of the cartridge buttress member 130, the tension being sufficient to maintain the cartridge buttress member 130 secured to the cartridge body 120. The secondary knife blade 170 includes a knife body 172 that is substantially L-shaped. The knife body 172 has blade 176 on a distal end portion thereof and a support arm 174 on a proximal end portion thereof. The support arm 174 extends laterally from the proximal end portion of the knife body 172 and defines a pair of opposed recesses 174*a* dimensioned to receive the pair of opposed nubs 164 (see FIGS. 4 and 5A) of the pusher member 160 to facilitate securement of the support arm 174 within the knife supporting slot 162*b* of the pusher member 160.

During operation of the surgical stapling device 10, the anvil assembly 200 and the cartridge assembly 100 are approximated by the actuation of advancing member 22 until the anvil assembly 200 and the cartridge assembly 100 are suitably clamped against tissue of a patient. The trigger member 24 is then actuated to fire the surgical stapling device 10. Reference may be made to U.S. Pat. No. 5,915,616 to Viola et al. and U.S. Patent Application Publication No. 2011/0174099 referred to above for a detailed description of the use of a surgical stapling device 10 in a surgical procedure.

With reference again to FIGS. 4 and 5A, upon a firing of the surgical stapling device 10, the pusher member 160 is distally advanced from the proximal position (FIG. 4) to the distal position (FIG. 5A) which drives the pushers 162*a* of the pusher member 160 through the fastener retaining slots 124 of the cartridge body 120 into engagement with the fasteners 60 to dispense the fasteners 60 from the fastener retaining slots 124.

The distal movement of the pusher member 160 drives the secondary knife blade 170 distally to sever the retaining ring member 140. Notably, with reference to FIG. 5B, to sever the retaining ring member 140, the secondary knife blade 170 advances distally through knife slot 156 of the stop member 150 and into engagement with a proximal surface of the cross member 158 of the stop member 150 which prevents further distal advancement of the secondary knife blade 170 after the blade 176 of the secondary knife blade 170 cuts through the retaining ring member 140. A distal surface of the stop member 150 including the cross member 158 prevents tissue from extruding in front of the secondary knife blade 170 when tissue is clamped between the anvil assembly 200 and the cartridge assembly 100 upon approximation of the anvil assembly 200 and the cartridge assembly 100.

Upon a severing of the retaining ring member 140, the securement tension imparted to the extension portion 134 of the cartridge buttress member 130 by the retaining ring member 140, prior to a severance of the retaining ring member 140, to secure the cartridge buttress member 130 to the cartridge assembly 100, is released. When the imparted tension is released, the extension portion 134 is freed so that when the device 10 is withdrawn from the surgical site, the cartridge buttress member 130 remains with the stapled tissue and is separated from cartridge body 120.

When the fasteners 60 are dispensed from the fastener retaining slots 124, the legs of the fasteners 60 are advanced through the clamped tissue and any buttress material clamped against tissue including the cartridge buttress member 130 and any buttress material that may supported on the anvil assembly. As the fasteners 60 are distally advanced, the legs of the fasteners are formed by fastener forming pockets defined in an anvil plate of the anvil assembly 200 to secure the buttress material including the cartridge buttress member 130 to the tissue.

Simultaneously or thereafter, the knife 52 is driven distally to sever the clamped tissue so that the buttress material is secured to tissue independent of the circular stapling apparatus 10.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

What is claimed is:

1. A circular stapling device, comprising:
   a handle assembly;
   an elongate body that extends from the handle assembly;
   a cartridge assembly mounted on a distal end of the elongate body, the cartridge assembly defining an annular containment groove, the cartridge assembly including:
     a housing;
     a pusher member supported within the housing and being movable between a first position and a second position; and
     a fastener cartridge body supported on the housing and having a tissue engaging surface that extends to an annular edge;
   a circular cartridge buttress member having a body portion and an extension portion, the body portion being supported on the tissue engaging surface of the fastener cartridge body, the extension portion extending from the body portion and over the annular edge of the tissue engaging surface; and
   a retaining ring member secured within the containment groove over the extension portion of the circular cartridge buttress member to releasably secure the circular cartridge buttress member to the fastener cartridge body.

2. The circular stapling apparatus of claim 1, further comprising a knife assembly, the knife assembly including a primary knife blade and a secondary knife blade, the primary knife blade dimensioned to cut tissue, the secondary knife blade being connected to the pusher member, the secondary knife blade being movable with the pusher member to cut the retaining ring member and relieve a tension that the retaining ring member exerts on the extension portion of the circular cartridge buttress member, the tension being sufficient to maintain the circular cartridge buttress member secured to the fastener cartridge body.

3. The circular stapling apparatus of claim 2, wherein the housing includes at least one containment tab that extends distally from a distal end portion of the housing so that an inner surface of the at least one containment tab is engageable with an outer surface of the retaining ring member to maintain the retaining ring member secured to the housing after the retaining ring member is cut with the secondary knife blade.

4. The circular stapling apparatus of claim 2, wherein the fastener cartridge body supports a stop member that defines a receiving channel dimensioned to receive the retaining ring member and a knife slot dimensioned to receive a distal end portion of the secondary knife blade, the stop member including a cross member dimensioned to prevent tissue from extruding in front of the distal end portion of the secondary knife blade, the distal end portion of the secondary knife blade being engageable with the cross member upon a translation of the distal end portion of the secondary knife blade through the knife slot.

5. The circular stapling apparatus of claim 4, wherein the stop member is formed of a polyethylene material.

6. The circular stapling apparatus of claim 1, wherein the retaining ring member is an o-ring.

7. The circular stapling apparatus of claim 6, wherein the o-ring is formed of an elastomeric material.

8. The circular stapling apparatus of claim 1, wherein the housing and the fastener cartridge body together define the containment groove therebetween.

9. A cartridge assembly, comprising:
  a housing;
  a pusher member supported within the housing and being movable between a first position and a second position; and
  a fastener cartridge body supported on the housing and having a tissue engaging surface that extends to an annular edge, wherein at least one of the housing and the fastener cartridge body define an annular containment groove;
  a circular cartridge buttress member having a body portion and an extension portion, the body portion being supported on the tissue engaging surface of the fastener cartridge body, the extension portion extending from the body portion and over the annular edge of the tissue engaging surface; and
  a retaining ring member secured within the containment groove to releasably secure the extension portion of the circular cartridge buttress member to the cartridge assembly.

10. The cartridge assembly of claim 9, wherein a knife blade is connected to the pusher member, the knife blade being movable with the pusher member to cut the retaining ring member and relieve a tension that the retaining ring member exerts on the extension portion of the circular cartridge buttress member, the tension being sufficient to maintain the circular cartridge buttress member secured to the fastener cartridge body.

11. The cartridge assembly of claim 10, further comprising a tissue cutting knife blade dimensioned to cut tissue.

12. The cartridge assembly of claim 9, wherein the housing includes at least one containment tab that extends distally from a distal end portion of the housing so that an inner surface of the at least one containment tab is engageable with an outer surface of the retaining ring member to maintain the retaining ring member secured to the housing.

13. The cartridge assembly of claim 10, wherein the fastener cartridge body supports a stop member that defines a receiving channel dimensioned to receive the retaining ring member and a knife slot dimensioned to receive a distal end portion of the knife blade, the stop member including a cross member dimensioned to prevent tissue from extruding in front of the distal end portion of the knife blade, the distal end portion of the knife blade being engageable with the cross member upon a translation of the distal end portion of the knife blade through the knife slot.

14. The cartridge assembly of claim 13, wherein the stop member is formed of a polyethylene material.

15. The cartridge assembly of claim 9, wherein the retaining ring member is an o-ring formed of elastomeric material.

* * * * *